United States Patent
Tets et al.

(10) Patent No.: US 10,624,892 B2
(45) Date of Patent: Apr. 21, 2020

(54) AGENT AGAINST FUNGAL INFECTIONS

(71) Applicants: Viktor Veniaminovich Tets, St. Petersburg (RU); Georgy Viktorovich Tets, St. Petersburg (RU)

(72) Inventors: Viktor Veniaminovich Tets, St. Petersburg (RU); Georgy Viktorovich Tets, St. Petersburg (RU)

(73) Assignees: Viktor Veniaminovich TETS, St. Petersburg (RU); Georgy Viktorovich TETS, St. Petersburg (RU)

( * ) Notice: Subject to any disclaimer, the term of this patent is extended or adjusted under 35 U.S.C. 154(b) by 0 days.

(21) Appl. No.: 15/750,089

(22) PCT Filed: Aug. 1, 2016

(86) PCT No.: PCT/RU2016/000499
§ 371 (c)(1),
(2) Date: Feb. 2, 2018

(87) PCT Pub. No.: WO2017/023193
PCT Pub. Date: Feb. 9, 2017

(65) Prior Publication Data
US 2018/0228805 A1    Aug. 16, 2018

(30) Foreign Application Priority Data
Aug. 4, 2015    (RU) ................................ 2015132513

(51) Int. Cl.
*A61K 31/513*    (2006.01)
*C07D 239/545*    (2006.01)
*A61P 31/10*    (2006.01)
*A61K 31/505*    (2006.01)

(52) U.S. Cl.
CPC .......... *A61K 31/513* (2013.01); *A61K 31/505* (2013.01); *A61P 31/10* (2018.01)

(58) Field of Classification Search
CPC ................ A61K 31/513; C07D 237/18; C07D 239/545; A61P 31/10
See application file for complete search history.

(56) References Cited

U.S. PATENT DOCUMENTS

| | | | |
|---|---|---|---|
| 3,361,745 A | 1/1968 | Schroeder et al. | |
| 6,730,787 B1 | 5/2004 | Krutikov et al. | |
| 8,987,277 B2 | 3/2015 | Tets et al. | |
| 9,895,371 B2 | 2/2018 | Tets et al. | |
| 2007/0027034 A1 | 2/2007 | Tank et al. | |
| 2010/0179204 A1 | 7/2010 | George et al. | |
| 2013/0261301 A1 | 10/2013 | Tets et al. | |

FOREIGN PATENT DOCUMENTS

| | | |
|---|---|---|
| EP | 2650285 A1 | 10/2013 |
| RU | 2198166 C2 | 2/2003 |
| RU | 2260590 C1 | 9/2005 |
| RU | 2448960 C1 | 4/2012 |
| RU | 2525911 C1 | 8/2014 |
| WO | 0034250 A1 | 6/2000 |
| WO | 2005/103014 A1 | 3/2005 |
| WO | 2008117037 A1 | 10/2008 |

OTHER PUBLICATIONS

International Search Report Issued for International Application No. PCT/RU2016/000499 and English Translation Thereof; 3 pages.
Berkengeim et al., "Chemistry and Technology of Synthetic Drugs" The Main Edition of the Chemical Literature, Moscow, 1935, p. 42, English Translation.
Communication (European Extended Search Report) issued in European Application No. 14896241.8 dated Dec. 7, 2017, 10 pages.
Communication (Extended European Search Report) dated Jun. 11, 2014, which issued during prosecution of European Application No. 11847307.3, 4 pages which corresponds to the present application.
Communication (Pursuant to Article 94) issued in European Patent Appln. No. 11847307.3 dated Mar. 3, 2016, 4 pages.
Group 1: Alkali Metals. Available from: http://web.archive.org/web/20080410115147/http://www.rsc.org/chemsoc/visualelements/pages/data/intro_groupi_data.html Published: Apr. 10, 2008, 3 pages total.
International Preliminary Report on Patentability dated Dec. 27, 2016, which issued in PCT/RU2014/000452, 6 pages.
International Preliminary Report on Patentability dated Jan. 18, 2013, which issued during prosecution of International Application No. PCT/RU2011/000140, 11 pages, which corresponds to the present application.

(Continued)

*Primary Examiner* — Emily A Bernhardt
*Assistant Examiner* — Laura M Daniel
(74) *Attorney, Agent, or Firm* — Troutman Sanders LLP

(57) ABSTRACT

The invention relates to fungicides and can be used for treating diseases caused by fungi, and also for preventing fungal damage to various materials and agricultural products. Claimed is an agent against fungal infections which is in the form of salts of 2,4-dioxo-5-arylideneamino-6-methyl-1,3-pyrimidine, where R is 4-NO$_2$, 2-OH-5-NO$_2$, 2-OH-3,5-Cl$_2$, 5-Br-4-OH-3-OCH$_3$, 2-OH-5-Cl, 2,4-Cl$_2$, 3,5-Br$_2$-2-OH. The result is an agent against fungal infections which has a broad spectrum of activity and is highly soluble, rendering it more effective for use in the form of solutions.

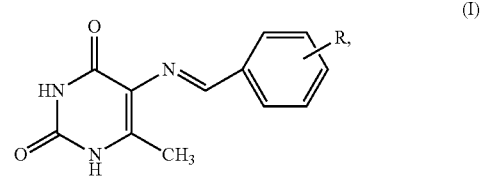

(I)

29 Claims, No Drawings

(56) References Cited

OTHER PUBLICATIONS

International Preliminary Report on Patentability issued by the International Searching Authority in International Application No. PCT/RU2016/000499 dated Feb. 6, 2018.

International Search Report dated Aug. 25, 2011, which issued during prosecution of International Application No. PCT/RU2011/000140, 10 pages, which corresponds to the present application.

International Search Report Issued in PCT/ RU2014/000452 dated Mar. 19, 2015; English Translation Thereof; 3 pages.

Krutikov, V.I. et al., "5-Arylideneaminouracils I. Synthesis and the Influence of Physico-Chemical Parameters on the Level of Biological Activity (5-Arilidenaminouratsily. I. Sintez, vliyanie fiziko-khimicheskikh parametrov na uroven biologicheskoy aktivnosti)" The Journal of General Chemistry (Zhurnal obschey khimii) (2009) vol. 79, Issue 5, pp. 813-818.

Krutikov, V.I., et al. "5-Arylideneaminouracils: II. Synthesis of Sodium and Ammonium Salts" Russian Journal of General Chemistry (2009) vol. 79, No. 5, pp. 991-995.

Tyukavkina, N.A. et al., "Bioorganic Chemistry (Bioogranicheskaya khimiya)" Moscow Drofa (2005) pp. 304-305.

Written Opinion issued by the International Searching Authority in International Application No. PCT/RU2016/000499 dated Jan. 12, 2017.

Written Opinion of the International Searching Authority dated Aug. 25, 2011, which issued during prosecution of International Application No. PCT/RU2011/000140, which corresponds to the present application.

Written Opinion of the International Searching Authority dated Mar. 19, 2015, which issued in International Application No. PCT/RU2014/000452, 12 pages; English Translation Thereof.

Yadav, A. V. et al., "Co-Crystals: A Novel Approach to Modify Physiochemical Properties of Active Pharmaceutical Ingredients", Indian Journal of Pharmaceutical Science (2009), pp. 359-370.

Yamashita, H. et al., "Coformer Screening Using Thermal Analysis Based on Binary Phase Diagrams", Pharmaceutical Research (2014), vol. 31, No. 8, pp. 1946-1957.

Indian Communication (First Examination Report (FER)) issued by the India Intellectual Patent Office in Indian Application No. 201817007775 dated Feb. 17, 2020, 5 pages total.

Brown, T.B. et al., "Triazines and related products. Part XV. 2,4-Diaminopyrimidines and 2-aminopyrimidin-4(3H)-ones bearing 1,2,3-benzotriazinyl groups as potential dihydrofolic reductase inhibitors" Journal of the Chemical Society, Perkin Transactions (1975) vol. 11, pp. 1023-1028.

AGENT AGAINST FUNGAL INFECTIONS

CROSS-REFERENCE TO RELATED APPLICATIONS

This application is a U.S. National Phase of International Patent Application No. PCT/RU2016/000499, filed on Aug. 1, 2016, which published as WO 2017/023193 A1 on Feb. 9, 2017, and claims priority to Russian Patent Application No. RU2015132513, filed on Aug. 4, 2015, all of which are herein incorporated by reference in their entirety.

TECHNICAL FIELD

The invention relates to agents against fungal infections and can be used for treating diseases caused by fungi, and also in agriculture and veterinary, as well as for prevention of fungal damage to various materials.

Treatment of fungal infections remains an unresolved, serious problem for the modern medicine, veterinary, crop production and industry. This is due to the inadequate efficacy of known agents, and the high variability of microbes leading to the emergence of stable forms (see Fidel P. L. Jr, Vazquez J. A., Sobel J. D. *Candida glabrata*: review of epidemiology, pathogenesis and clinical disease with comparison to *C. albicans* 1999, 1:80-96. White T. Antifungal agent resistance in *Candida albicans* ASM News 8:427-433).

BACKGROUND ART

A number of agents for the treatment of fungal diseases are known from the prior art: Nystatin, Amphotericin B, Fluconazole, Terbinafine (Dixon D M, Walsh T J. Antifungal Agent on the World Wide Web at ncbi.nlm.nih.gov/books/NBK8263/?report=reader).

Each of them has significant drawbacks. Fluconazole shows mainly fungistatic effect and, in practice, does not exhibit fungicidal properties. [Pharmaceutical microbiology. Ed. by W. B. Hugo and A. D. Rassel Blackwell Scientific Publications, Oxford, 1987, 511 p]. The foregoing makes it difficult to use these agents to treat people with a weakened immune system. Fluconazole can also be used to prevent fungal damage to plants and agricultural products. Fluconazole is also known to be used in archive-keeping for paper treatment.

The main disadvantage of nystatin is its low activity against multicellular fungi.

Amphotericin B is an active antifungal agent; however, it is highly toxic and causes a number of serious side effects.

All these agents have been used for many years and various bacteria have developed resistance to them (see A. Kanafani1 J. R. Perfect2Resistance to Antifungal Agents: Mechanisms and Clinical Impact Clinical Infectious Diseases 2008:46 120-126).

A fungicidal agent is known from prior art which is an associate of 5-[3,5-dichloro-2-hydroxybenzylidene)amino]-4-hydroxy-1H-pyrimidin-2-one salt with 1,2,3,4,5-pentahydroxy-6-methylaminohexane

CH$_3$NHCH$_2$CH(OH)CH(OH)CH(OH)CH(OH)CH$_2$OH

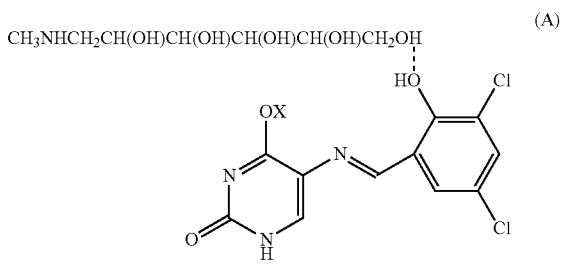

(A)

where X=Na, K, NH$_4^+$, RU 2525911 C1, publ. 20 Aug. 2014.

This technical solution is adopted as a prototype of the present invention.

The agent exhibits a pronounced antifungal activity of a broad spectrum.

However, this substance is poorly soluble in both aqueous medium and in fats. The solubility of the known preparation in water does not exceed 0.4%, and in oil solutions it is up to 0.3%. Insufficient solubility of the prototype fungicidal agent does not allow obtaining stable solutions suitable for practical use. At the same time, the problem of increasing the effectiveness of use of the fungicidal agent in solution form for applications in medicine and veterinary in the form of inhalations and injections, as well as for treatment of various materials and agricultural products, is extremely relevant.

SUMMARY OF THE INVENTION

It is an object of the present invention to provide an effective agent against fungal infections with a broad spectrum of activity and a higher solubility.

According to the invention, the above object is achieved by the synthesis of a fungicidal agent which is 2,4-dioxo-5-arylideneamino-6-methyl-1,3-pyrimidine.

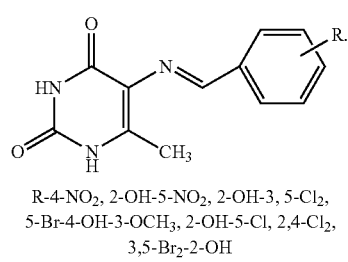

(I)

R-4-NO$_2$, 2-OH-5-NO$_2$, 2-OH-3, 5-Cl$_2$,
5-Br-4-OH-3-OCH$_3$, 2-OH-5-Cl, 2,4-Cl$_2$,
3,5-Br$_2$-2-OH

The values of R are given in Table 1.

The applicant is not aware of any sources of information that would contain information about identical technical solutions, which makes it possible to conclude that the claimed invention complies with the criterion of "Novelty" ("N").

Through the implementation of the claimed technical solution, the technical result is achieved, which consists in provision of an effective agent against fungal infections with a broad spectrum of activity and a higher solubility.

The applicant has not found any sources of information containing data on the effect of the distinctive features of the invention on the technical result achieved due to their implementation.

The abovementioned circumstances make it possible to conclude that the claimed technical solution conforms to the "Inventive Step" (IS) criterion.

BRIEF DESCRIPTION OF THE DRAWINGS

In the following, the invention is explained with a detailed description of examples of its implementation without reference to the drawings.

PREFERRED EMBODIMENT

The structure of the obtained compounds was proved by spectra of proton magnetic resonance and IR spectroscopy.

The desired salts of 2,4-dioxo-5-arylideneamino-6-methyl-1,3-pyrimidine are prepared by reacting the sodium salt of 5-amino-6-methyluracil with aromatic aldehydes. As a solvent, a 3:1 ethanol-water mixture was used. The products were obtained with yields above 80% of the theoretical value. The individuality of the target compounds was proved by thin layer chromatography: the system of eluents—chloroform-acetone 3:1. The melting temperature of the products is over 300° C.

Example 1: Synthesis of 2,4-dioxo-5-(4-nitrobenzylidene)amino-6-methyl-1,3-pyrimidine sodium salt (I-1)

0.5 g of 5-amino-6-methyluracil and 0.5 ml of a 50% solution of sodium hydroxide were placed in a flask. The mixture was heated with stirring until the initial material dissolved completely. In parallel, 0.18 ml of ethanol was dissolved in 0.6 g of 4-nitrobenzaldehyde and added to a solution of 5-amino-6-methyluracil, while a precipitate of burgundy-red color began to form in the flask. The reaction mixture was then stirred for 30 minutes and cooled. The resulting precipitate was filtered off, washed with ethanol and dried. The product yield was 83% of the theoretical value.

Example 2: Synthesis of 2,4-dioxo-5-(2-hydroxy-3,5-dichlorobenzylidene) amino-6-methyl-1,3-pyrimidine sodium salt (I-3)

1.41 g of 5-amino-6-methyluracil and 0.4 g of sodium hydroxide in 10 ml of water were placed into the reaction flask. The mixture was heated up to complete dissolution of the original uracil. At the same time, 1.91 g of 3,5-dichlorosalicyl aldehyde was dissolved in 30 ml of ethanol, and the resulting solution was added dropwise to the solution of sodium salt of 5-amino-6-methyluracil, while stirring. The reaction mass was heated with stirring for 1 hour, then cooled to room temperature, and the formed precipitate was filtered off, washed with ethanol and dried. The yield of the desired product was 2.86 g (85%).

Example 3. Treatment of Respiratory Diseases

The studies were conducted on white mongrel mice (females, 6-8 weeks) in Rappolovo (Leningrad region), the quarantine period was 2 weeks.

To reproduce *aspergillus* pneumonia of the mouse, in order to create an immunodeficiency, a cyclophosphamide solution (150 mg/kg) was injected once intraperitoneally. Three days later, the mice were injected hydrocortisone (250 mg/kg), intraperitoneally, once. One day after the hydrocortisone administration the mice were infected with a suspension of *Aspergillus niger* (approximately $3 \times 10^7$ cell/ml) intranasally, under ether anesthesia.

On the 5th day after infection, 5 animals from each group were taken to study microbial contamination of the lungs (euthanasia in rodents was performed with an overdose of ether). From the lung tissue, homogenates were prepared in which the titer of *Aspergillus* genus fungi was determined. Observation over the remaining mice was carried out within 14 days after infection for mortality accounting.

The test solutions were injected in an aerosol chamber.

In the course of the experiment, the following groups of animals were formed:

1—spray control (K), 3 identical groups (K1, K2, K3). The animals infected with *Aspergillus* and receiving an aerosol of isotonic sodium chloride solution.
2—The associate of 5-[3,5-dichloro-2-hydroxybenzylidene)amino]-4-hydroxy-1H-pyrimidin-2-one salt with 1,2,3,4,5-pentahydroxy-6-methylaminohexane, 3 identical groups (E1-3). The animals infected with *Aspergillus* and receiving an aerosol of 0.1% of the preparation under study.
3. Aqueous solution of substance I-1
4. Aqueous solution of substance I-2
5. Aqueous solution of substance I-3
6. Aqueous solution of substance I-4
7. Aqueous solution of substance I-5
8. Aqueous solution of substance I-6
9. Aqueous solution of substance I-7.

Experimental Setup

The animals were placed into aerosol chambers (12 l) for a period of 30 minutes, during which 500 ml of air passed through the lungs.

As an aerosol generator, an ultrasonic nebulizer OMRON U1 (Japan) was used. To maintain a constant concentration of the aerosol of the preparation in the chamber, a vortex pneumatic generator in pulsed spraying mode was used to obtain a stable aerosol with a particle size of 3 m. The animals were placed into immobilization containers and exposed to the obtained aerosol for 30 minutes once a day for 3 days, starting from the first day after the infection.

Results.

From the samples of homogenized lung tissues, a number of successive dilutions were prepared, followed by seeding on to Saburo medium. The results are shown in Table 2.

Thus, under the conditions used, the most effective antifungal agent was Substance I-3.

Example 4. Candidamycosis of Mammals Caused by *Candida albicans*

Rabbits were inoculated intradermally with a suspension of a 48-hour *Candida albicans* culture at a dose of 10,000 fungal cells in 500 l of a 0.9% sodium chloride solution. After 7-10 days, a part of the animals exhibited ulceration at the injection site; they were used for the experiment.

For the study, a 0.1% oil (olive oil) solution of the 5-[3,5-dichloro-2-hydroxybenzylidene)amino]-4-hydroxy-1H-pyrimidin-2-one salt associate with 1,2,3,4,5-pentahydroxy-6-methylaminohexane and substance I-3 were prepared.

Sterile water was used as the control substance.

The duration of treatment was 7 days, starting from the $1^{st}$ day after ulceration. The preparations were applied with a cotton swab twice a day—in the morning and in the evening.

The criterion for mycological cure was the absence of the yeast and mycelial forms of *Candida*, and the criterion for complete cure was the scarring of the lesion by day 7.

The results are shown in Table 3.

Thus, a positive effect is achieved only with the use of Substance I-3.

Example 5. Treatment of Fungal Infections in Plants

The study was carried out on *begonia tuberosa* (*Begonia tuberosa hybridum*), infected with powdery mildew. Powdery mildew affects many plants, including trees and shrubs. Powdery mildew affects chrysanthemums, begonias, and roses; it is manifested in appearance of a white, sometimes darkening spew on green parts of plants. The plant disease is transmitted by spores through the air.

The test plants were infected with spores of the fungus (*Leveillula taurica*) and kept until a white spew appeared on the leaves. Three leaves on each plant were infected. After appearance of the spew, the plants of the control group (3 plants) were isolated from the 3 plants treated with a spray, which is an aqueous solution of substance I-3. The treatment was performed once in a day for 3 and 7 days. After completion of the treatment, the observation over the plants was continued for another 3 weeks. During the observation, an increase in the amount of spew representing the fungal mycelium was registered in the control plants and the number of affected leaves increased, on average, to 7-8, while the spew covered the stems of the plants as well. In plants treated with the substance under study, no increase or spread of the fungus to other parts of the plant was recorded. When flushed from the leaf and plated on a nutrient medium, no growth of the fungi was recorded.

INDUSTRIAL APPLICABILITY

The invention is implemented using common materials and equipment, resulting, according to the applicant's opinion, in compliance of the invention with the "Industrial Applicability" ("IA") patentability criterion.

TABLE 1

Characteristics of the target compounds of general formula 1

| Number of compound | R | Chemical - formula | Yield, % | $R_f$ |
|---|---|---|---|---|
| I-1 | 4-NO$_2$ | C$_{12}$H$_{10}$N$_4$O$_4$Na | 83 | 0.12 |
| I-2 | 2-OH-5-NO$_2$ | C$_{12}$H$_{10}$N$_4$O$_5$Na | 85 | 0.14 |
| I-3 | 2-OH-3,5-Cl$_2$ | C$_{12}$H$_9$Cl$_2$N$_3$O$_3$Na | 88 | 0.18 |
| I-4 | 5-Br-4-OH-3-OCH$_3$ | C$_{13}$H$_{12}$BrN$_3$O$_4$Na | 86 | 0.22 |
| I-5 | 2-OH-5-Cl | C$_{12}$H$_{10}$ClN$_3$O$_3$Na | 87 | 0.18 |
| I-6 | 2,4-Cl$_2$ | C$_{12}$H$_9$Cl$_2$N$_3$O$_2$Na | 84 | 0.04 |
| I-7 | 3,5-Br$_2$-2-OH | C$_{12}$H$_9$Br$_2$N$_3$O$_3$Na | 86 | 0.3 |

TABLE 2

Results of successive dilutions were prepared, followed by seeding on to Saburo medium.

| Groups of animals | Number of colonies (in different dilutions) | | |
|---|---|---|---|
| | $10^{-2}$ | $10^{-4}$ | $10^{-6}$ |
| Control -1 | 49 col | 3 col | — |
| Control -2 | 85 col | 3 col | — |
| Control -3 | 63 col | 1 col | — |
| The associate of 5-[3,5-dichloro-2-hydroxybenzylidene)amino]-4-hydroxy-1H-pyrimidin-2-one salt with 1,2,3,4,5-pentahydroxy-6-methylaminohexane-1 | 12 col | 2 col | — |
| Substance I-1 | 5 col | — | — |
| Substance I-2 | 6 col | 1 col | — |
| Substance I-3 | 2 col | — | — |
| Substance I-4 | 6 col | 1 col | — |
| Substance I-5 | 7 col | 2 col | — |
| Substance I-6 | 4 col | — | — |
| Substance I-7 | 5 col | 1 col | — |

TABLE 3

Results of treatment Candidamycosis of mammals

| Preparation | Presence of mycelium of fungi in the smear | | Complete cure by day 7 |
|---|---|---|---|
| | 3 day | 5 day | |
| Control | +++ | +++ | Absent |
| The associate of 5-[3.5-dichloro-2-hydroxybenzylidene)amino]-4-hydroxy-1H-pyrimidin-2-one salt with 1,2,3,4,5-pentahydroxy-6-methylaminohexane | +++ | ++ | Absent |
| Substance I-3 | + | no growth | Achieved |

The invention claimed is:

1. A compound of formula (I):

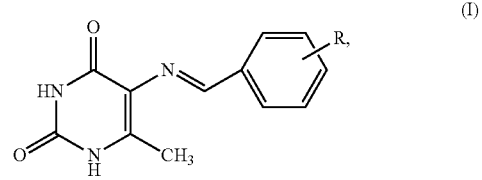

(I)

wherein R is selected from 4-NO$_2$, 2-OH-5-NO$_2$, 2-OH-3,5-Cl$_2$, 5-Br-4-OH-3-OCH$_3$, 2-OH-5-Cl, 2,4-Cl$_2$, and 3,5-Br$_2$-2-OH, or a pharmaceutically acceptable salt thereof.

2. The compound of claim 1, wherein R is 4-NO$_2$.

3. The compound of claim 1, wherein R is 2-OH-5-NO$_2$.

4. The compound of claim 1, wherein R is 2-OH-3,5-Cl$_2$.

5. The compound of claim 1, wherein R is 5-Br-4-OH-3-OCH$_3$.

6. The compound of claim 1, wherein R is 2-OH-5-Cl.

7. The compound of claim 1, wherein R is 2,4-Cl$_2$.

8. The compound of claim 1, wherein R is 3,5-Br$_2$-2-OH.

9. The compound of claim 1, which is a sodium salt of the compound of formula (I).

10. A composition comprising the compound of claim 1 and a carrier.

11. The composition of claim 10, wherein the carrier is water.

12. The composition of claim 10, wherein the carrier is an oil.

13. The composition of claim 12, wherein the carrier is olive oil.

14. A pharmaceutical dosage form comprising the compound of claim 1 and a pharmaceutically acceptable carrier.

15. The pharmaceutical dosage form of claim 14, wherein the dosage form is suitable for administration by inhalation.

16. The pharmaceutical dosage form of claim 14, wherein the dosage form is suitable for topical administration.

17. The pharmaceutical dosage form of claim 14, wherein the dosage form is in the form of a spray.

18. The pharmaceutical dosage form of claim 14, wherein the dosage form is in the form of a solution.

19. A method for preventing or inhibiting growth of a fungus comprising administering an effective amount of the compound of claim 1.

20. The method of claim 19 wherein the fungus is from a genus selected from *Candida, Aspergillus, Malassezia*, and *Leveillula*.

21. The method of claim 20, wherein the fungus is from a species selected from *Candida auris, Candida glabrata, Aspergillus niger*, and *Leveillula taurica*.

22. A method for preventing or inhibiting growth of a fungus comprising administering an effective amount of the composition of claim 10.

23. A method for treating a fungal infection in a subject in need thereof comprising administering to the subject an effective amount of the compound of claim 1.

24. The method of claim 23, wherein the fungal infection is a respiratory infection or a skin infection.

25. The method of claim 23, wherein the fungal infection is selected from fungal pneumonia, candidamycosis, and powdery mildew.

26. The method of claim 23, wherein the fungal infection is pneumonia caused by a *Candida* fungus.

27. The method of claim 23, wherein the fungal infection is pneumonia caused by *Candida auris* or *Candida glabrata*.

28. A method for treating a fungal infection in a subject in need thereof comprising administering to the subject an effective amount of the composition of claim 10.

29. A method for treating a fungal infection in a subject in need thereof comprising administering to the subject the pharmaceutical dosage form of claim 14.

\* \* \* \* \*